United States Patent [19]

Kleemann et al.

[11] Patent Number: 4,824,987
[45] Date of Patent: Apr. 25, 1989

[54] METHOD OF PREPARING M-TRIFLUOROMETHYLPHENYL ACETONITRILE

[75] Inventors: Axel Kleemann, Mühlheim; Herbert Klenk, Hanau; Klaus Huthmacher, Gelnhausen; Dieter Most, Bruchköbel, all of Fed. Rep. of Germany

[73] Assignee: Degussa Aktiengesellschaft, Frankfurt-Main, Fed. Rep. of Germany

[21] Appl. No.: 197,343

[22] Filed: May 23, 1988

[30] Foreign Application Priority Data

May 23, 1987 [DE] Fed. Rep. of Germany ....... 3717434

[51] Int. Cl.$^4$ ............................................. C07C 120/00
[52] U.S. Cl. .................................... 558/348; 558/332
[58] Field of Search ................................ 558/332, 348

[56] References Cited

U.S. PATENT DOCUMENTS

| | | | |
|---|---|---|---|
| 2,553,404 | 5/1951 | Dixon | 558/348 |
| 2,606,917 | 8/1952 | Dixon | 558/348 X |
| 3,417,126 | 12/1968 | Taguchi et al. | 558/348 |
| 3,683,003 | 8/1972 | Aufdereggen et al. | 558/348 |
| 3,994,984 | 11/1976 | Kidwell | 570/211 |
| 4,144,265 | 3/1979 | Dowd et al. | 558/344 |
| 4,369,322 | 1/1983 | Schalke et al. | 558/332 X |
| 4,390,706 | 6/1983 | Kleemann et al. | 558/332 X |

OTHER PUBLICATIONS

DE-3717434-C1, Kleemann et al., Patentschrift, 9-1-5-88, 2 pp. spec., no drawing.
Pavlath et al.; Aromatic Fluorine Compounds, pp. 54-55 (date unknown).

Primary Examiner—Joseph Paul Brust
Attorney, Agent, or Firm—Cushman, Darby & Cushman

[57] ABSTRACT

A method of preparing m-trifluoromethylphenyl acetonitrile of the formula

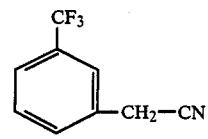

in which m-trifluoromethyl toluene is reacted with cyanogen chloride in the gas phase at 600° to 750° C.

4 Claims, No Drawings

METHOD OF PREPARING M-TRIFLUOROMETHYLPHENYL ACETONITRILE

The present invention relates to a new method of preparing m-trifluoromethylphenyl acetonitrile.

BACKGROUND OF THE INVENTION

M-trifluoromethylphenyl acetonitrile is a compound which is used as a starting material for the preparation of a plurality of drugs and herbicides. It was previously prepared, for example, by reacting m-trifluoromethyl benzene with chloromethyl ether in the presence of chlorosulfonic acid and treating the reaction product further with sodium cyanide (see U.S. Pat. No. 4,144,265). When this method is used, the desired compound could only be obtained in a yield of 31%, relative to the benzene trifluoride. Furthermore, the process had the following additional disadvantages:

The cost of preparation is considerable (two-stage process), particularly in the case of first stage in which the chloromethylation of benzotrifluoride (deactivated aromate), involves substantial problems. For example, the handling of the charges chlorosulfonic acid and chloromethyl ether, especially during the aqueous work-up of the raw product, entails considerable problems since further purification steps are necessary in order to remove the carcinogenic chloromethyl ether (see U.S. Pat. No. 3,994,984). The question of waste removal is also critically evaluated. In particular, the formation of by-products limits the yield, e.g. various chloromethylated products or the formation of condensation products such as bis-(3-trifluoromethylphenyl) methane.

It is also known that m-trifluoromethylphenyl acetonitrile can be prepared by first subjecting trifluoromethyl benzene to a chloromethylation and then reacting it according to the Kolbe nitrile synthesis with sodium cyanide (See Published German Patent specification DE-OS No. 21 50 399). However, this method has the following disadvantages:

Since a two-stage method is involved, the cost of preparation is also very high here. For example, the first stage in particular, involves the chloromethylation of benzotrifluoride (deactivated aromate), which entails considerable problems. If chlorosulfuric acid is brought into p-formaldehyde (see U.S. Pat. No. 3,465,051), a viscous, adhesive mass results initially which can be stirred only with difficulty and which causes considerable technical problems. In addition to the work-up, the formation of by-products is especially critical since up to 30% bis-(3-trifluoromethylphenyl) methane is formed according to this method. This results in a distinct reduction of the yield.

It is known from published German Patent Specification DE-PS No. 28 54 210 (corresponding to U.S. Pat. No. 4,369,322) that aromatically or heteroaromatically substituted acetonitriles can be obtained by reacting methyl-substituted aromates or heteroaromates with cyanogen chloride in the gas phase at temperatures approximately between 550° and 850° C.; however, this method has never been applied in the past to m-trifluoromethyl toluene because fragmentations, especially the splitting off of $.CF_3$ and $.CH_3$ and exchange reactions, fluorine for chlorine/cyanide, were feared. A possible HF formation would have destroyed the reactor and the work-up part as a consequence.

SUMMARY OF THE INVENTION

It has now been found that m-trifluoromethylphenyl acetonitrile can be prepared in yields over 80%, relative to m-trifluoromethyl toluene, if m-trifluoromethyl toluene is reacted with cyanogen chloride in the gas phase at a temperature between 600° and 750° C. In view of knowledge of published German Patent Specification DE-PS No. 28 54 210 (corresponding to U.S. Pat. No. 4,369,322), as discussed above, it was thus quite surprising that m-trifluoromethylphenyl acetonitrile is accessible in this manner.

It is advantageous in this process to use the m-trifluoromethyl toluene and the cyanogen chloride in a molar ratio of 3:1. However, it is possible to use the m-trifluoromethyl toluene in an excess up to 8:1.

The method is preferably performed at a temperature of approximately 650° C.

It is advantageous to proceed in such a manner when performing the method of the invention that the two reactants are fed into the reactor in a gaseous state and separated from one another. The two reactants should have already been preheated nearly to the reaction temperature upon entering into the reactor. The work-up of the reaction products can be performed in a known manner, e.g. by means of distillation.

The dwell times in the reactor should be approximately 10–50 seconds.

The m-trifluoromethyl toluene used as starting material can be prepared e.g. according to the method described in European Pat. No. 0,084,128 by reacting e.g. benzotrifluoride with an alkylation agent in the presence of hydrogen fluoride in a temperature range of 0° to 150° C.

The following examples illustrate the invention.

EXAMPLE 1

2.11 moles of 3-trifluoromethyl toluene and 0.38 mole of cyanogen chloride (molar ratio 5.6:1) are passed through a silica tube (diameter 3.6 cm, length 100 cm) which was heated in an electric furnace. The average temperature of the reaction tube was 650° C., the contact time 12.7 sec. The hot reaction gases are subsequently condensed at 90° to 95° C. so that readily volatile by-products such as hydrochloricacid gas, unreacted cyanogen chloride, etc. are expelled and supplied to a detoxification unit.

A gas-chromatographic analysis of the raw product showed a yield of 3-trifluoromethylphenyl acetonitrile of 80.8% (relative to 3-trifluoromethyl toluene),
55.3% (relative to cyanogen chloride).

The reaction product (boiling point 92° to 93° at 4 mm Hg) can be separated by means of a fractionating distillation from unreacted 3-trifluoromethyl toluene (boiling point 131° to 133° at 760 mm Hg) without appreciable distillation losses.

The identification was performed spectroscopically (with reference substances).

EXAMPLE 2

0.40 mole of 3-trifluoromethyl toluene and 0.125 mole of cyanogen chloride (molar ratio 3.2:1) were reacted under the same conditions as in Example 1. The average temperature of the reactor tube was 650° C., the contact time 40 sec. A gas-chromatographic analysis of the raw product showed a yield of 3-trifluoromethylphenyl acetonitrile of 72.7% (relative to 3-trifluoromethyl toluene),
64.0% (relative to cyanogen chloride).

EXAMPLE 3

0.40 mole of 3-trifluoromethyl toluene and 0.125 mole of cyanogen chloride (molar ratio 3.2:1) were reacted under the conditions described in Example 1. The average temperature of the reactor tube was 700° C., the contact time was 38 sec. A gas-chromatographic analysis of the raw product displayed a yield of 3-trifluoromethylphenyl acetonitrile of
53.3% (relative to 3-trifluoromethyl toluene),
64.0% (relative to cyanogen chloride).

EXAMPLE 4

2.11 moles of m-trifluoromethyl toluene and 0.38 mole of cyanogen chloride (molar ratio 5.6:1) were reacted under the conditions described in Example 1. The average temperature of the reactor tube was 700° C., the dwell time was 12.2 sec. A gas-chromatographic analysis of the raw product showed a yield of 3-trifluoromethylphenyl acetonitrile of
70.5% ( relative to 3-trifluoromethyl toluene),
81.6% (relative to cyanogen chloride).

What is claimed is:

1. A method of preparing m-trifluoromethylphenyl acetonitrile of the formula:

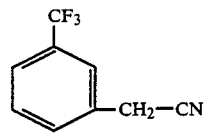

which comprises reacting m-trifluoromethyl toluene with cyanogen chloride in the gas phase at a temperature between 600° and 750° C.

2. A method according to claim 1 in which the m-trifluoromethyl toluene is added in an excess up to 8:1.

3. A method according to claim 2 in which the m-trifluoromethyl toluene and the cyanogen chloride are added in a molar ratio of 3:1.

4. A method according to any one of claims 1 to 3 in which the reaction is performed at a temperature of approximately 650° C.

* * * * *